United States Patent [19]

Nakada

[11] Patent Number: 4,648,399
[45] Date of Patent: Mar. 10, 1987

[54] RESECTOSCOPE
[75] Inventor: Akio Nakada, Hachioji, Japan
[73] Assignee: Olympus Optical Co., Ltd., Japan
[21] Appl. No.: 685,314
[22] Filed: Dec. 24, 1984
[30] Foreign Application Priority Data Jan. 9, 1984 [JP] Japan ............................... 59-1044[U]

[51] Int. Cl.⁴ ............................................ A61B 17/36
[52] U.S. Cl. ............................................... 128/303.14
[58] Field of Search ........... 128/303.1, 303.13, 303.14,
128/303.15, 303.17, 311, 4, 6

[56] References Cited

U.S. PATENT DOCUMENTS

| 2,545,865 | 3/1951 | Wallace | 128/303.15 |
| 3,294,085 | 12/1966 | Wallace | 128/303.15 |
| 4,423,727 | 1/1984 | Wildran et al. | 128/303.15 |
| 4,427,006 | 1/1984 | Nottke | 128/303.17 |

Primary Examiner—Willam E. Kamm
Attorney, Agent, or Firm—Ostrolenk, Faber, Gerb & Soffen

[57] ABSTRACT

A resectoscope includes an electrode which is effective to resect an affected part by cauterization upon energization with high frequency current. A slider element is slidable lengthwise of the resectoscope and includes an electrode receiving hole in which an electrical terminal is mounted. The proximal end of the electrode is inserted into the hole and secured to the terminal. Thus the electrode is fixed to the slider and can be moved back and forth with respect to the resectoscope's body. An elastic seal member having an internal diameter less than the external diameter of an insulation coat on the electrode is located in the opening into the hole to prevent water droplets or blood from entering into the hole.

3 Claims, 4 Drawing Figures

RESECTOSCOPE

BACKGROUND OF THE INVENTION

The invention relates to a resectoscope, and more particularly, to an improvement of an electrode receiving hole of a resectoscope.

A resectoscope is generally designed for direct insertion into the bladder through the urethra to effect excision of an affected part, for example, the prostate with an electrode which is energized with high frequency current. The resectoscope permits visual observation of the prostate while it is being treated,. A conventional resectoscope is illustrated in FIG. 1 and comprises an optical sight tube 1, an electrode 2, a resect-sheath 3 through which the tube 1 and the electrode 2 pass, a handle 4 attached to the sheath 3 toward its proximal end, and a slider 5 which is used to secure the rear end of the electrode 2 in place. The sliding movement of the slider 5 allows the electrode to be moved back and forth.

FIG. 2 shows a part of the slider 5 where the electrode is attached. Specifically, the slider 5 is formed with an electrode receiving hole 6 having an energizing terminal 7 mounted at its innermost location therein, to which the electrode 2 is secured. However, it is found that during a high frequency treatment with the electrode 2 in a surgical operation, water droplets, blood or the like may find its way into the hole 6, whereupon the high frequency current may leak through such fluid to a metallic portion of the resectoscope, giving rise to the likelihood that an operator may get burnt when he touches the metallic portion. It is also possible that a discharge or flashover may occur from the area of hole 6 to any surrounding metals. Such discharge disadvantageously causes a fired solidification of the blood or other fluids, presenting a marred appearance. Furthermore, the resulting fired products contributed to the enhanced deposition of water droplets thereon, which in turn forms additional discharge paths, thus increasing the chance of discharge even more.

SUMMARY OF THE INVENTION

It is an object of the invention to prevent the ingress of fluid such as water droplets or blood into an electrode receiving hole of a resectoscope.

In accordance with the invention, the inlet of the electrode receiving hole of the resectoscope is provided with a seal member, which prevents the ingress of fluid such as water droplets or blood, thus avoiding the leakage of high frequency current.

Thus, according to the invention, the inlet of the electrode receiving hole is provided with a seal member in the form of an O-ring, for example, thus preventing the ingress of fluid such as water droplets or blood into the hole during the surgical operation. This effectively prevents leakage of the high frequency current, avoiding the likelihood that an operator may get burnt. At the same time, discharge to any surrounding metals and the resulting formation of fired products of blood deposited on the handle of the resectoscope are eliminated. The absence of fired products avoids discharge paths which may otherwise be created by water droplets deposited thereon.

DESCRIPTION OF PREFERRED EMBODIMENT

Figure 1:
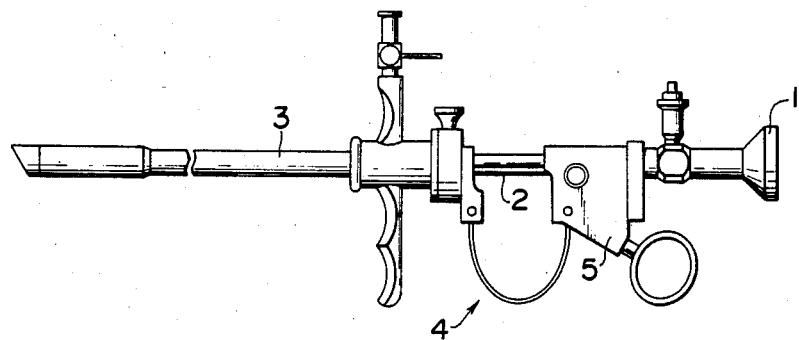
FIG. 1 is a side elevation of an exemplary resectoscope of the prior art.
Figure 2:
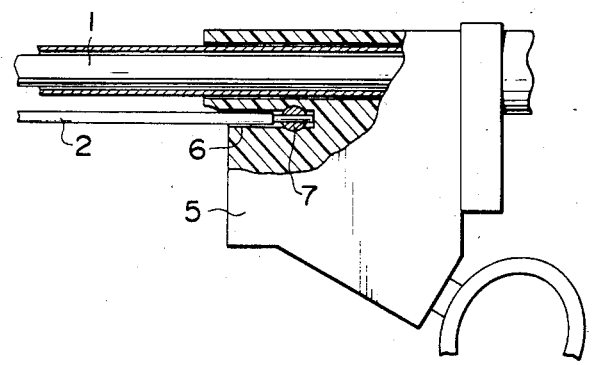
FIG. 2 is a fragmentary enlarged view, partly in cross section, of the resectoscope shown in FIG. 1.
Figure 3:
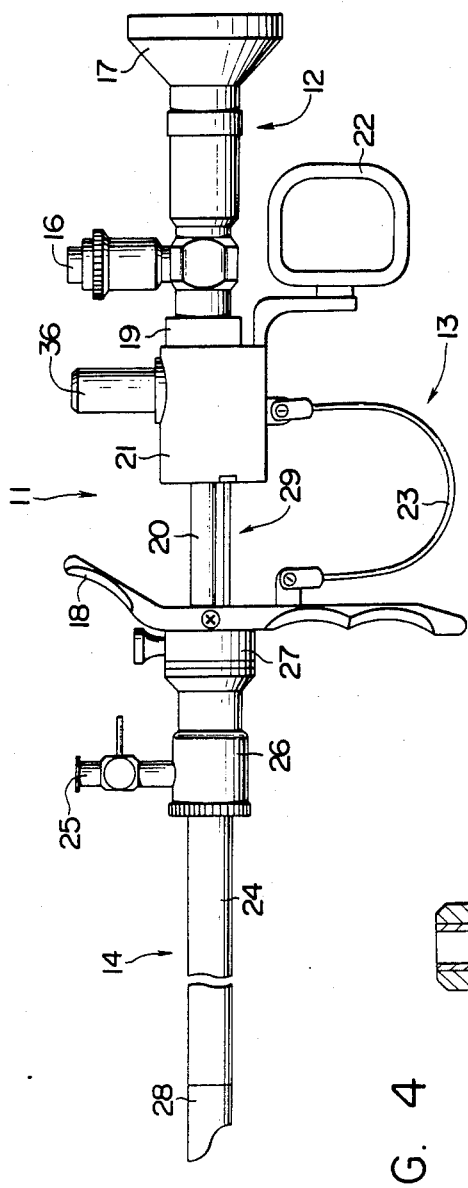
FIG. 3 is a side elevation of a resectoscope according to one embodiment of the invention.

Referring to FIG. 3, there is shown a resectoscope 11 constructed according to one embodiment of the invention. It comprises an optical sight tube 12, a resecto-handle 13 which permits the sight tube to be inserted thereinto or withdrawn therefrom, and a resecto-sheath 14 which is mounted on the resecto-handle 13 in a detachable manner.

The optical sight tube 12 includes a portion 15 (see FIG. 4) adapted to be inserted into the urethra and internally housing a light guide and an image transmitting optical system, both not shown, a light guide connector 16 located at the rear end of the portion 15 and laterally extending therefrom, and an eyepiece assembly 17 mounted on the rear end of the portion 15. The handle 13 includes a finger piece 18 located forwardly of and connected to a block 19 by a guide pipe 20 through which the inserted portion 15 extends. The block 19 permits the sight tube 12 to be detachably connected therewith at its rear end. The handle 13 also includes a slider 21 formed of an insulating materials such as plastic materials and which is axially slidable along the guide pipe 20. It will be noted that the slider 21 is formed with a thumb ring 22. A leaf spring 23 is connected between the finger piece 18 and the slider 21.

The resecto-sheath 14 includes a portion 24 formed of a metal such as stainless steel and adapted to be inserted into the physical body, a sheath body 26 carrying a feedwater mouthpiece 25 and connected to the proximal end of the portion 24, and a sheath connector 27 which is integral with the rear end of the sheath body 26 and which can be detachably connected to the finger piece 18 of the handle 13. The inserted sheath portion 24 has a distal end portion 28 which is formed of an insulating material such as epoxy resin or ceramics.

Figure 4:
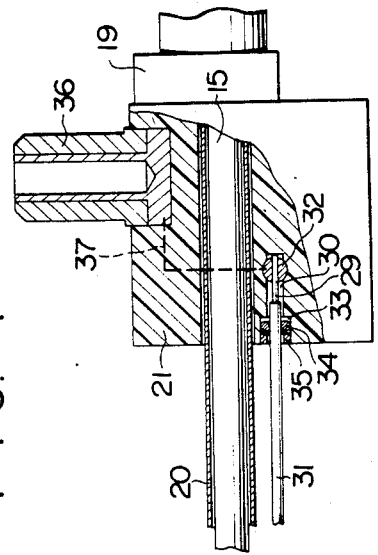
FIG. 4 is a fragmentary enlarged view, partly in cross section, of the resectoscope shown in FIG. 3.

The resecto-sheath 14 has an internal passage, through which the guide pipe 20 of the handle 13, having the inserted portion 15 disposed therein as illustrated in FIG. 4, extends to the proximity of the distal end portion 28. An electrode 29 is disposed within the passage in juxtaposition with the guide pipe 20. While not shown, it is to be understood that the distal end of the electrode 29 is formed into a loop which serves the resecting purpose. The proximal end of the electrode 29 is located in an electrode receiving hole 30 formed in the slider 21. The electrode 29 is covered with an insulative coat 31 except for its proximal and distal ends. At its innermost end, the hole 30 is provided with an energizing terminal 32, which is constructed to enable the proximal end of the electrode 29 to be secured therein. The inlet of the electrode receiving hole 30 is defined as a recess 33, in which an O-ring 34 is secured by means of a clamp 35 of an insulating material. The O-ring 34 has an internal diameter which is less than the external diameter of the insulative coat 31 on the electrode 29, thus maintaining the water tightness. The energizing terminal 32 is electrically connected to a cord fixture 36 fixed in the slider 21 through a lead wire 37, which is schematically shown by broken lines.

In operation, when resecting an affected part by the use of the resectoscope 11 through which high frequency current is passed, the proximal end of the electrode 29 is inserted into the hole 30 in the slider 21 until it reaches the inner end of the hole, whereby the end not covered by the coat 31 is secured in and electrically connected to the energizing terminal 32. Since the internal diameter of the O-ring 34 is less than the external diameter of the insulative coat 31, water tightness is maintained by the O-ring 34 over a region secured to the terminal 32, preventing the ingress of fluid such as water or blood into the hole 30 during the surgical operation. Since the terminal 32 is electrically connected to the fixture 36 through the lead wire 37, the connection of the fixture 36 with a source of high frequency current through a cord, not shown, enables the loop formed at the distal end of the electrode 29 to resect an affected part.

What is claimed is:

1. A resectoscope for resecting an object, comprising:
   a longitudinally elongate resectoscope body;
   a sheath portion for insertion into the object to be resected;
   a slider including an electrode hole and an electrical terminal fixed in said electrode hole;
   means for mounting the slider for longitudinal movement with respect to said sheath portion; said means spacing said slider from a proximal end of said sheath portion;
   an electrode having a proximal end which is secured within said electrical hole and a distal end and a resecting element located at said distal end, the resecting element being for resecting an affected part of the object upon application of an appropriate current to said electrode; and
   an elastic seal means disposed in an inlet of said electrode hole abutting said electrode for elastically sealing said hole so as to make said hole water tight and prevent fluid spray droplets induced by passing high frequency current through said electrode from creating an electrical short between a noninsulated portion of said electrode within said electrode hole and a further noninsulated portion of the resectoscope.

2. A resectoscope according to claim 1, in which said elastic seal means comprises an O-ring securely affixed in said electrode hole.

3. A resectoscope according to claim 1, in which said seal means has an opening through which said proximal end of said electrode passes, said opening having an internal diameter which is less than an external diameter of said insulation coat at the location where said seal means abuts said electrode.

* * * * *